US011904066B2

(12) United States Patent
Rosenblat et al.

(10) Patent No.: US 11,904,066 B2
(45) Date of Patent: *Feb. 20, 2024

(54) SANITIZATION DEVICE FOR GROCERIES OR OTHER OBJECTS

(71) Applicants: Heath Rosenblat, Poughkeepsie, NY (US); Margarita Ginzburg, Far Hills, NJ (US)

(72) Inventors: Heath Rosenblat, Poughkeepsie, NY (US); Margarita Ginzburg, Far Hills, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/717,244

(22) Filed: Apr. 11, 2022

(65) Prior Publication Data

US 2022/0233736 A1    Jul. 28, 2022

Related U.S. Application Data

(63) Continuation of application No. 16/904,180, filed on Jun. 17, 2020, now Pat. No. 11,324,846.

(51) Int. Cl.
*A61L 2/26* (2006.01)
*A61L 2/10* (2006.01)

(52) U.S. Cl.
CPC .......... *A61L 2/26* (2013.01); *A61L 2/10* (2013.01); *A61L 2202/11* (2013.01); *A61L 2202/122* (2013.01); *A61L 2202/16* (2013.01)

(58) Field of Classification Search
None
See application file for complete search history.

(56) References Cited

U.S. PATENT DOCUMENTS

| 9,657,177 | B1 | 5/2017 | Pringle et al. |
| 10,232,067 | B2 * | 3/2019 | Kim .......................... A61L 2/10 |
| 10,357,043 | B2 | 7/2019 | Rizzo et al. |
| 11,324,846 | B2 * | 5/2022 | Rosenblat ............... A61L 2/202 |

(Continued)

FOREIGN PATENT DOCUMENTS

KR    101017596 B1 *  2/2011

OTHER PUBLICATIONS

Cheng et al. ("Inactivation of Listeria and *E. coli* by Deep-UV LED: effect of substrate conditions on inactivation kinetics". Sci Rep 10, 3411 (2020). https://doi.org/10.1038/s41598-020-60459-8).*

*Primary Examiner* — Andrew Smyth
(74) *Attorney, Agent, or Firm* — Leason Ellis LLP

(57) ABSTRACT

A sanitizer using radiation comprises a hollow housing with an aperture, the housing being generally opaque to the radiation utilized. Mounted to the interior surfaces of the housing are radiation sources that produce radiation when powered. In operation, multiple objects to be sanitized are placed within the interior and the radiation sources powered, thereby sanitizing by radiation any pathogens present on the objects be irradiated. An easily adjustable shelving system that is substantially non-opaque to the radiation utilized, such as wire shelving with minimal opaque surfaces, may be used to support the objects to be sanitized. Depending on size, the portable box allows for multiple objects to be sanitized at the same time. The sanitizer in certain embodiments includes a plurality of UVC radiation sources mounted in the interior of the housing so as to surround the object to be sanitized on multiple sides.

5 Claims, 5 Drawing Sheets

(56) References Cited

U.S. PATENT DOCUMENTS

| | | | |
|---|---|---|---|
| 2007/0094841 A1* | 5/2007 | Jo | A47L 5/14 |
| | | | 15/346 |
| 2007/0274879 A1 | 11/2007 | Millikin | |
| 2010/0044582 A1 | 2/2010 | Cooper et al. | |
| 2010/0148090 A1 | 6/2010 | Chang | |
| 2014/0203188 A1 | 7/2014 | Yerby | |
| 2018/0361001 A1* | 12/2018 | Liao | A61L 2/24 |
| 2019/0099509 A1* | 4/2019 | Martz | A61L 2/24 |
| 2020/0150040 A1* | 5/2020 | Gross | G01N 21/6447 |

* cited by examiner

SANITIZATION DEVICE FOR GROCERIES OR OTHER OBJECTS

TECHNICAL FIELD

Embodiments of the invention relate to portable devises for irradiating and sanitizing the outer wrappings or packaging of groceries, wine bottles, cardboard boxes, or other objects while in transit from a grocery store or other location to home in a safe and controlled environment. Embodiments of the present invention relate to sterilization, e.g., using UVC radiation, ozone, etc., and, more particularly, to the use of such sterilization in both fixed and portable box-type sanitizers.

BACKGROUND OF THE INVENTION

In general, pathogens such as bacteria and viruses are everywhere within our environment, including on, for example, door handles, counter tops, shopping cart and basket handles, checkout conveyors, public floors, sidewalks, and in the air. Currently, there exist many solutions for cleaning hands from germs, such as hand sanitizer, wet wipes, etc. These products may help people who are on the go or who want a quick solution to cleaning their hands when washing with soap and water is not an option. It is not, however, feasible nor convenient to use chemical wipes and/or cleaning solutions on all grocery or product packaging surfaces that need to be sanitized. And even when more convenient logistically, it is also time consuming to wipe down every product or object acquired from a store and then to clean the area where the objects were placed, such as the kitchen countertop or floor.

Disinfection from germs or other pathogens from grocery packaging or other objects is generally done using sanitizer, wet wipes, soap and hot water, bleach or bleach equivalent and similar products that require a consumer to spend time carefully wiping or washing and drying packaging of each item, placing the package from a contaminated surface to a clean surface, repeating the process for multiple items, cleaning the contaminated surface on which the packages were originally placed and storing the cleaned and wiped packages in their intended location such as the refrigerator or pantry. Some packaged items lend themselves well to wiping or washing (e.g., milk bottle) while others do not (e.g., cereal box or bread in paper packaging). This is also a time consuming, imperfect, and tedious process especially when done by a single individual without the assistance of a second "clean" person to process the cleaned items efficiently.

Aside from chemical wipes and other cleaning solutions, short-wavelength ultraviolet (UVC) light is a proven and effective way to remove bacteria, viruses, and other pathogens. UVC sanitizers are well known for use in sterilizing all manner of objects including contact lenses, combs, cell phones, safety goggles and other small items. Often only a single source of radiation is employed and, as such, there are often areas on an object to be sanitized that are shadowed from the UVC radiation produced from the single source. Current UVC options for removing germs/bacteria are often expensive and are not readily accessible to the average consumer and/or often have a singular specific use. Furthermore, there are risks with UVC light. For example, UVC light may cause skin cancer and/or cataracts when exposed to the user. Therefore, a need exists for a device that is safe for humans and may be used to sanitize surfaces, such as grocery packaging, in a quick, easy, safe manner, to eliminate pathogens in a form factor that is readily available and accessible for everyday use by the average consumer.

In light of the aforementioned drawbacks and limitations, there exists a need for a portable or mobile device for use in a vehicle, which may also be fixed at a residence, for providing quick and safe sterilization of outer wrappings or packaging of groceries, wine bottles, cardboard boxes, or other objects while in transit from the point of acquisition of said objects to the home with minimal activity involved by the user. Such devices may advantageously be used to substantially sanitize multiple objects at the same time. Devices that satisfy this unmet need may further use minimal irradiation or sterilization to provide a quick and effective method for preventing the spread of viruses, bacteria or other pathogens without endangering the safety of the user.

SUMMARY OF THE INVENTION

Embodiments of the present invention provide systems and methods for the quick, safe, and portable sterilization of the outer wrappings or packaging of groceries, wine bottles, cardboard boxes, or other objects that may be deployed for use within the trunk of a vehicle. Fixed deployments are also contemplated for home use. The systems and methods for sanitizing disclosed herein may be used on the outer wrappings or packaging of groceries, wine bottles, cardboard boxes, or other objects after they have been on the shelves of a grocery store, stocked by store employees and exposed to airborne pathogens from other customers, a grocery cart or basket, the grocery conveyor belt, checkout clerk, etc.

Embodiments of the present invention are directed towards a box-type-portable sanitizer using C-band Ultra-Violet (100-280 nm) ("UVC") radiation that comprises a hollow rectangular box that defines a volume with a door on one end such as the top. The box may comprise hollow ¼ inch construction of all walls, including the top and bottom. Other embodiments comprise solid wall construction without any space or gap between inner and outer walls. Mounted facing the interior volume of the box are, according to one embodiment, a plurality of strategically placed 275 nm UVC LED SMD 3535 Deep LED Diode UV Chip or similar UVC radiation LEDs, UVC radiation bulbs, or similar UVC lightings that, when powered, are each operative to generate UVC radiation. Such UVC lights may be mounted between the walls of the box such that a given UVC light emits UVC radiation through one or more openings in the interior wall of the box. Affixed to the bottom of the box may be a plurality of wheels to allow for easy movement of the sanitizing box. Alternatively, such wheels may be housed within the bottom interior wall (or a cavity formed therethrough or therein) for deployment by the user as needed, e.g., "pop out" wheels.

Shelves may be used within the box to hold items for sterilization apart from one another and thereby achieve sterilization of increased surface area of the goods. Shelves may comprise minimally opaque components for placement within the volume that the interior of the box defines into which a user may locate an object(s) to be irradiated and sanitized. According to some embodiments, the upper shelves are height adjustable with an easy click-in/rail system basket design. In operation, an object (or multiple objects) to be irradiated and sanitized may be placed inside the box, the door closed, and the lights powered for one or more periods of time such that any pathogens present on the object(s) to be sanitized are irradiated by the UVC radiation. Shelves with minimal opaque structures are used to support the object(s) to be sanitized and separate the object(s) to be sanitized from the lamps, as well as each other, thereby allowing the UVC radiation to pass between and fully bathe the objects. In accordance with mobile embodiments, the device is configured to utilize typical 12-volt DC power that can be obtained by, e.g., (i) plugging into a cigarette lighter/ USB adapter of a vehicle trunk or interior of vehicle through a trunk pass through; (ii) plugged into an external battery power attachment; (iii) a wall outlet; and/or (iv) hard wired into a vehicle electric system, etc.

According to one embodiment, a sanitizer using radiation comprises a hollow housing with an aperture, the housing being generally opaque to the radiation utilized. Mounted to the interior surfaces of the housing are radiation sources that produce radiation when powered. In operation, multiple objects to be sanitized are placed within the interior and the radiation sources powered, thereby sanitizing by radiation any pathogens present on the objects be irradiated. An easily adjustable shelving system that is substantially non-opaque to the radiation utilized, such as wire shelving with minimal opaque surfaces, may be used to support the objects to be sanitized. Depending on size, the portable box allows for multiple objects to be sanitized at the same time. The sanitizer in certain embodiments includes a plurality of UVC radiation sources mounted in the interior of the housing so as to surround the object to be sanitized on multiple sides.

According to another embodiment of the present invention, the system comprises a 12-volt DC powered, portable opaque box that defines an interior volume to receive groceries or other objects. Positioned on the interior of the box and operative to irradiate objects contained within the interior volume of the portable opaque box are one or more ultraviolet lights, which according to one embodiment are germicidal 275 nm UVC LED SMD 3535 Deep LED Diode UV Chips or similar UVC radiation LEDs, UVC radiation bulbs, or similar UVC lightings that properly allow the UVC light wavelengths to reach the outer surfaces of the objects for maximum germicidal effectiveness. A number of shelves or trays are disposed within the volume to as to support the items for sterilization, for example, one (1) full size, removable, thin yet durable, easy-to-clean shelf (such as epoxy-coated steel or other non-corrosive UVC/ozone stable materials) with a minimal amount of opaque coverage in a pattern for maximum exposure of the objects to UVC light on the bottom of the box set at specified height with legs and handles and two (2) half size, removable, adjustable, thin yet durable, easy-to-clean shelves (such as epoxy-coated steel or non-corrosive UVC/ozone stable materials) with a minimal amount of opaque coverage in a pattern for maximum exposure of objects to UVC light. Embodiments further comprise a timer and safety mechanism (such a as magnetic switch that must indicate closure of a lid to the box prior to and during operation) to ensure the device is not operational unless the device is securely closed. A control board with a timer display and software is deployed to control the time of use for maximum effectiveness and safety cut off control.

According to still further embodiments of the present invention, the system comprises a 12-volt DC powered, portable opaque box, e.g., constructed of HDPE or other UVC/ozone stable material, to receive and strategically position groceries or other objects within the main body of the portable opaque box. Within the interior of the box are one or more 12V 10 g/h ceramic Ozone generator(s), e.g., located at the bottom of the box, to allow air sterilization and germicidal action to reach the outer surfaces of the packaging and therefore provide maximum germicidal effectiveness. According to certain embodiments, contained within the volume are one (1) full size, removable, thin yet durable, easy-to-clean, shelf with a minimal amount of opaque coverage in a pattern for maximum exposure of objects to ozone and set at specified height with legs and handles, and two (2) half size, removable, adjustable, durable, easy-to-clean, shelves with a minimal amount of opaque coverage in a pattern for maximum exposure of objects to ozone. A timer and safety mechanism to ensure the device is not operational unless the device is securely closed. A control board with a timer display and software is deployed to control the ozone generation time of use for maximum effectiveness and in accordance with any proscribed safety requirements.

According to another embodiment of the present invention, a method of irradiating and sanitizing the outer wrappings or packaging of groceries, wine bottles, cardboard boxes, or other objects over a period of time comprises the steps of: placing the objects inside the portable opaque box, which may be kept inside a vehicle trunk or at a fixed location, on shelves in a configuration that allow for the irradiating agent to come into contact with surfaces of the objects; engaging a safety switch to ensure operation only while the box is securely closed, and setting a time to control the amount of time over which the objects in the portable opaque box are irradiated.

In accordance with another aspect of the present invention there is provided a sanitizer apparatus. The sanitizer comprises a hollow rectangular box, which may be made from ¼ inch diameter sealed walls, defining an interior having six surfaces covered in a material that is opaque to UVC radiation to the outside of the box and may reflect UVC light back into the interior of the box and a door providing a re-sealable closure for an access aperture in one of said six surfaces. The aperture allows for placement of multiple objects to be sanitized within the interior. A bottom UVC radiation source may be mounted facing the interior of the box in said interior of said housing with a support structure of set and/or adjustable shelves mounted in said interior of said housing above said bottom UVC radiation sources, said support structure provided to support said objects to be irradiated and sanitized. A plurality of UVC radiation sources may be positioned and mounted in the interior of the box so as to be facing the interior of the box, irradiating, and surrounding said objects in UVC light for sanitization. Such UVC radiation sources may be placed in a space that may exist in a space between the walls comprising the box with the UVC radiation source positioned through said spaces.

According to still further embodiments of the present invention, the method of irradiating and sanitizing the outer wrappings or packaging of groceries, wine bottles, cardboard boxes, or other objects over a period of time comprises the steps of: placing the objects inside the portable opaque box, which is kept inside a vehicle trunk or at a fixed location, on shelves in a configuration that allow for ozone to come into contact with surfaces of the objects; engaging a safety switch to ensure operation only while the box is securely closed, and setting a time to control the amount of time over which the objects in the portable opaque box are exposed to an ozone generation source. The method may further comprise locking the box for a period of time subsequent to operation of the ozone generation source so as to provide sufficient disinfecting of the objects contained therein.

DETAILED DESCRIPTION OF THE EMBODIMENTS

Throughout the present specification, the technical terms and abbreviations are to be interpreted in the broadest sense of the respective terms, and include all similar items in the field known by other terms, as may be clear to persons skilled in art. Restriction or limitation if any referred to in the specification, is solely by way of example and for understanding the present invention. Also, there is no stringent rule as far as the visual layout of the apparatus is concerned. While the drawings display the different embodiment, the invention would cover all other variants that seek to achieve the same object as that of the present invention.

In different exemplary embodiments, the systems and methods described herein are directed towards portable devices and methods for providing sanitization while in transit or at home of the outer wrappings or packaging of groceries, wine bottles, cardboard boxes, or other objects. The process of disinfecting objects with UVC light requires that the object be exposed to the correct wavelength of UVC light for a period of time. The interior of a vehicle trunk in conjunction with the portable box set forth herein, provides an excellent platform through which to accomplish the disinfection process while completing point-to-point travel (or stationary if additional items need to be disinfected after the completion of disinfecting a first batch). The interior of the home or garage is an acceptable location for the device as well. 12-volt DC power is supplied via a vehicle charger, e.g., cigarette to USB adapter, an external battery supply, a hard-wired adapter kit for the vehicle or a regular power plug may suffice for providing power to the essential components as explained in connection with the exemplary embodiments.

Figure 1:
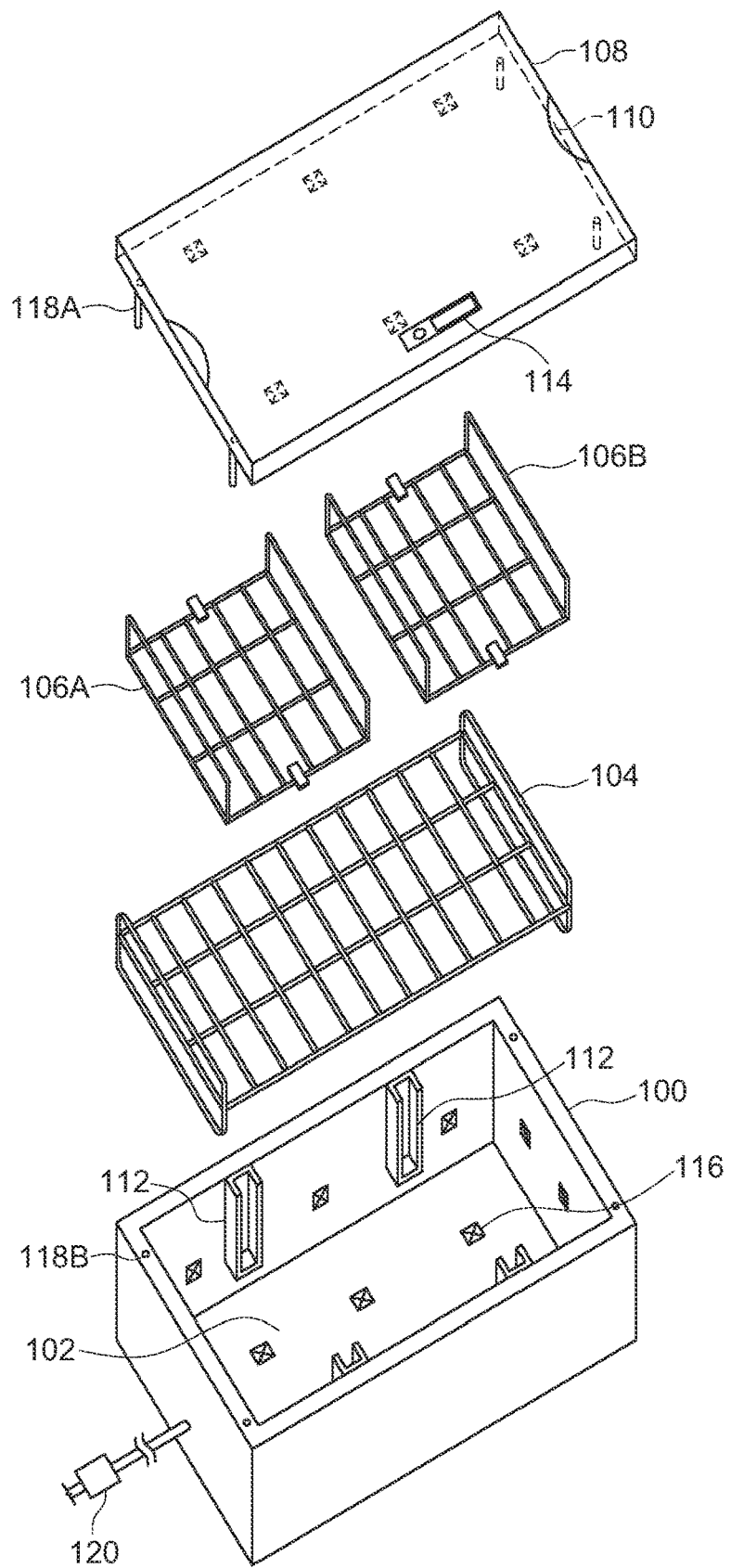
FIG. 1 illustrates an exploded perspective view of a portable sanitizing box system in accordance with one embodiment of the present invention.

FIG. 1 illustrates an exploded view of a sanitization box in accordance with one embodiment of the present invention that is operative to sanitize the outer wrappings or packaging of groceries, wine bottles, cardboard boxes, or other objects. Such sanitization, as is explained in greater detail herein, can be provided by a number of mechanisms including, but not limited to, UVC sterilization, ozone sterilization, etc. The sanitizing box in accordance with the embodiment of FIG. 1 comprises a housing having left and right sides, front and back sides, and top and bottom sides, thereby forming an opaque box 100. According to one embodiment, the box 100 is constructed of hollow ¼ inch walls made of High-density polyethylene ("HDPE") or other similar material that is opaque to UVC radiation and UVC stable. Other embodiments comprise solid wall construction without any space or gap between inner and outer walls. Advantageously, the material may be coated with an adhesive and a UVC reflective material applied to the inside surface.

The box 100 may be sized so as to accommodate multiple packages or other items by receiving them through a top removable door 108, which may be configured with side indentations 110 to allow for easy lifting and access to the interior volume 102 of the box 100. The interior volume 102 of the box 100 may be outfitted with one or more shelves 104, 106A and 106B that may be removable and adjustable and may further be substantially UVC transparent. Also, embodiments allow for height adjustment by providing a rail system 112 for certain shelves so as to accommodate certain objects based on surface area to be irradiated and sanitized, yet optimized to allow any given sanitization agent, e.g., UVC light, ozone, etc., to achieve contact with the maximum amount of surface area.

According to the embodiment of FIG. 1, the box 100 is compact such that it can fit easily inside the trunk of an average vehicle. Alternative embodiments are directed towards larger sizes for crossover, SUV, or home use, as well as the use of a side opening door rather than top opening door. The opaque box 100 with its top door 108 creates a closed environment in which the objects can be sanitized inside a normal vehicle trunk, for example, through the application of UVC light or ozone. The box 100 may house all the major components of the sanitizing system, although embodiments that distribute certain subsystems outside the box 100 are contemplated as falling within the scope of the present invention.

To control operation of the sanitization mechanism, the box 100 implements electronics 114 that include a timer mechanism that controls timing of the release and distribution of sanitizing agent within the box. In one embodiment, electronics 114 further comprise a control module in communication with the timer such that for the duration of the timer counting down to a zero time the control module executes program code, which may be embedded code, to control operation of an array of 275 nm UVC LED SMD 3535 Deep LED Diode UV Chips, UVC radiation LEDs, UVC radiation bulbs, or similar UVC lightings 116 that are disposed within the interior volume of the box, which may comprise disposing one or more lights on the door 108 of the box 100. The UVC LEDs 116 may, alternatively comprise cold cathode UVC germicidal lamps with optional ozone lamps (not shown) or any other suitable unbreakable UVC lamps. Similarly, where the sanitizing agent is ozone, the control module executes program code to control operation of, e.g., a 12V 10 g/h ceramic ozone generator.

In an exemplary embodiment of the present invention, the portable disinfection box 100 as depicted in FIG. 1 comprises a set of no less than sixteen (16) 275 nm UVC LED SMD 3535 Deep LED Diode UV Chips, UVC radiation LEDs, UVC radiation bulbs, or similar UVC lightings 116, which are placed at periodic locations on each internal surface of the box 100. In certain embodiments, such array of UVC LED lights 116 are mounted between the opaque walls of the box 100 and facing the interior through corresponding openings so as to allow the lights to irradiate the objects on the interior 102. UVC reflective material may be used to cover the interior 102 walls of the opaque box 100 and serve as an aid to the dispersal of the UVC radiation within the box 100. In one embodiment of the present invention, the UVC reflective material is polished aluminum diamond plate or UVC reflective coating identified in U.S. Pat. No. 9,657,177, which is hereby incorporated by reference in its entirety, to reflect any UVC radiation that reaches an interior surface 102 of the box 100 back toward the object to be sanitized. As will be apparent to a person of ordinary skill in the art, with these or other highly-reflective interior surfaces, the UVC LEDs 116 need not necessarily be mounted proximate to all six interior surfaces of the sanitizer 100 and, instead, a fewer number interior surfaces may suffice. The UVC radiation, coupled with structural environment inside the apparatus, thus promotes germicidal action by eliminating viruses and other pathogens through irradiation.

The use of shelving 104, 106A and 106B, by various embodiments of the invention helps promote such germicidal activity. For example, the embodiment of FIG. 1 comprises one (1) lower 104 and two (2) upper shelves or racks 106A and 106B for holding objects to be sanitized. The lower shelf 104 may be supported by feet at a specified height, as well as be removable with handles for easy clean up. In the present embodiment, the upper two shelves 106A and 106B are half the size of the bottom shelf 104 with a rail/basket design 112 to keep the objects contained. Each basket is attached to a set of adjustable rails 112 with an easy clip in system that locks in place when desired height is reached—this provides stability and allows for upward adjustment or removal with an upward pull motion. A given set of rails 112 are embedded into the box 100 and firmly supported to handle the weight of the objects affixed to them.

The shelves 104, 106A and 106B, may be comprised of thin metal wire design with minimum opaque elements that allows for maximum exposure of the grocery packaging or other objects to the UVC light wavelengths. While there is no limit to the size and number of objects that can be placed in the box 100 other than the maximum volume of the box interior 102 and proper closing of the lid 108, it is important to note that in order to properly disinfect the packaging or outer wrapper of a given object, such packaging or outer wrapper needs to be exposed to the disinfectant, e.g., UVC light or ozone. Accordingly, it is important for the object to be located on the provided shelves 104, 106A and 106B with space between them and not stacked on top of each other, which has the undesirable effect of preventing surfaces from achieving sufficient exposure to the disinfectant.

As further illustrated in the embodiment of FIG. 1, the box 100 comprises a door 108, which here is a top door, although various embodiments may utilize other door configurations. The door 108 comprises a safety mechanism and may also implement a lock that secures the box 100 during sanitization. The safety mechanism 118A and 118B may be one or more safety contacts/switches 118A in communication with corresponding contacts 118B on the box 100 that together are utilized to ensure a closed environment respectively for the safe operation of the device. Although embodiments allow for the door 108 to be fully removable for ease of shelf 104, 106A and 106B adjustment and placement of objects into the box 100, the device is not operable without the door 108 being fully closed. If the door 108 is opened when the sanitizer is in use, i.e., when the UVC LEDs 116 are receiving power from a power source 120, the door safety mechanism 118A and 118B may interrupt power 120 to the UVC LEDs 116. This is beneficial, since it is known that accidental exposure to UVC radiation can cause corneal or other severe burns. The electronic components described herein may be disposed within an electronic compartment in the door 108 that is provided with an access door to provide for maintenance.

An optional component for inclusion as part of the sanitization box 100 is the use of a lamp monitor (not pictured) that measures the output of UVC lights that might be used for sterilization. During exposure, the lamp monitor may measure and provide an indication to the user of the power output of the UVC LEDs 116. This feature may be useful where the power output of the UVC LEDs 116 diminishes. As the power output of the UVC lamps 116 diminish, it is necessary to increase the duration of exposure of an object to be sanitized to radiation from the UVC LEDs 116 to properly sanitize the object. Consequently, according to the indication of power output provided by the lamp monitor, the operator may set the timer appropriately for the next set of objects to be sanitized. A person of ordinary skill in the art should be able to determine a necessary duration of radiation from the amount of radiation per unit time indicated by the lamp monitor and the desired amount of radiation to which is it is desired to expose the objects to be sanitized. Additionally, the lamp monitor may be configured to indicate when the power output of the UVC lamps 116 has diminished to a level below a predetermined threshold. Such an indication may be interpreted as a sign that one or more of the UVC lamps need to be changed.

By way of exemplary operation when utilizing UVC radiation, objects to be sanitized is placed in the interior 102 of the sanitizer box 100. The top door 108 is closed, the UVC LEDs 116 are switched on, and the objects to be sanitized are bathed in UVC radiation. Due to the placement of UVC LEDs 116 on many, if not all, of the interior 102 sides of the sanitizer box 100, very little of the surface area of the objects to be sanitized are shadowed from the UVC radiation. Additionally, the objects to be sanitized are supported upon the specially located shelves, 104, 106A and 106B, which are designed to engage in minimal blockage of the UVC radiation, and, therefore, do not significantly shadow the objects to be sanitized from the UVC radiation.

By way of further description of the exemplary operation, an operator of the sanitizer box 100 opens a door 108 to the box 100, which may comprise unlocking a door lock that is operative to secure the door 108 and opens the sanitizer box 100 to expose the interior volume thereof 102. The operator may place objects to be sanitized upon the bottom shelf 104 with space between the objects, adjusting the top shelves, 106A and 106B, and placing the objects thereon in a desired configuration, followed by securing a door lock when present. The operator may then use the electronics 114, specifically the timer, to select a desired duration of exposure and activate master power 120 to power the sanitizing mechanism, e.g., UVC LEDs or ozone generator. When the selected duration of exposure expires, the master power 120 may be automatically powered off. The user may then open the door 108 to expose and remove the objects, which may now be considered to be sanitized.

Thus the individual components, as explained above in connection with the various exemplary embodiments, tend to perform their own specific function for the sanitization process that, in combination with the portable sanitization box 100, creates a micro-environment inside a regular vehicle trunk, SUV, crossover, or other vehicle, home or other location, to sanitize multiple objects at the same time in a very easy, safe and convenient manner Additionally, those skilled in the art will understand that the shape of the housing is not necessarily limited to that of a rectangular box. Other shapes, such as spherical and conical, may also be useful in certain applications.

Figure 2:
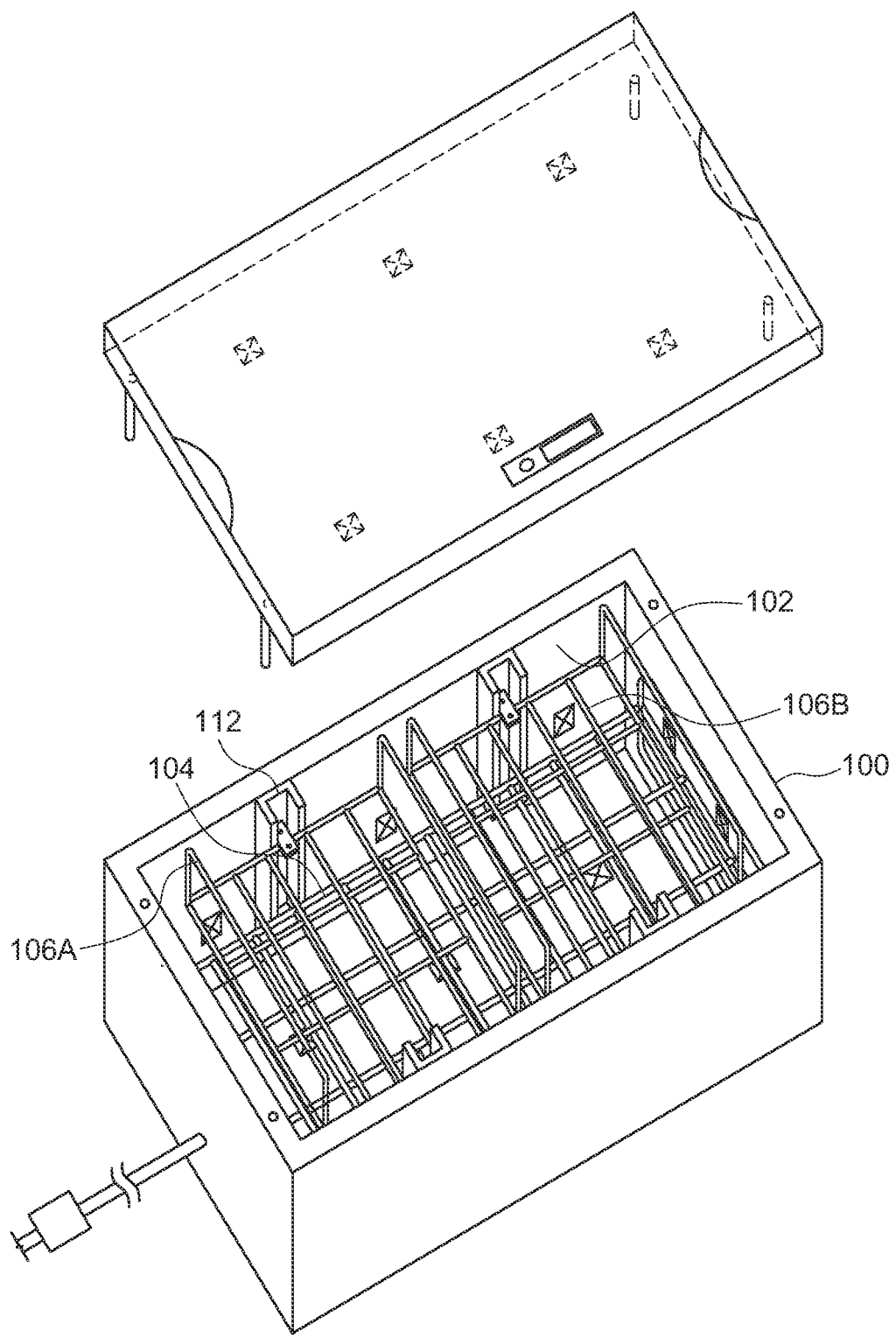
FIG. 2 illustrates a partially constructed perspective view of a portable sanitizing box system in accordance with one embodiment of the present invention.
Figure 3:
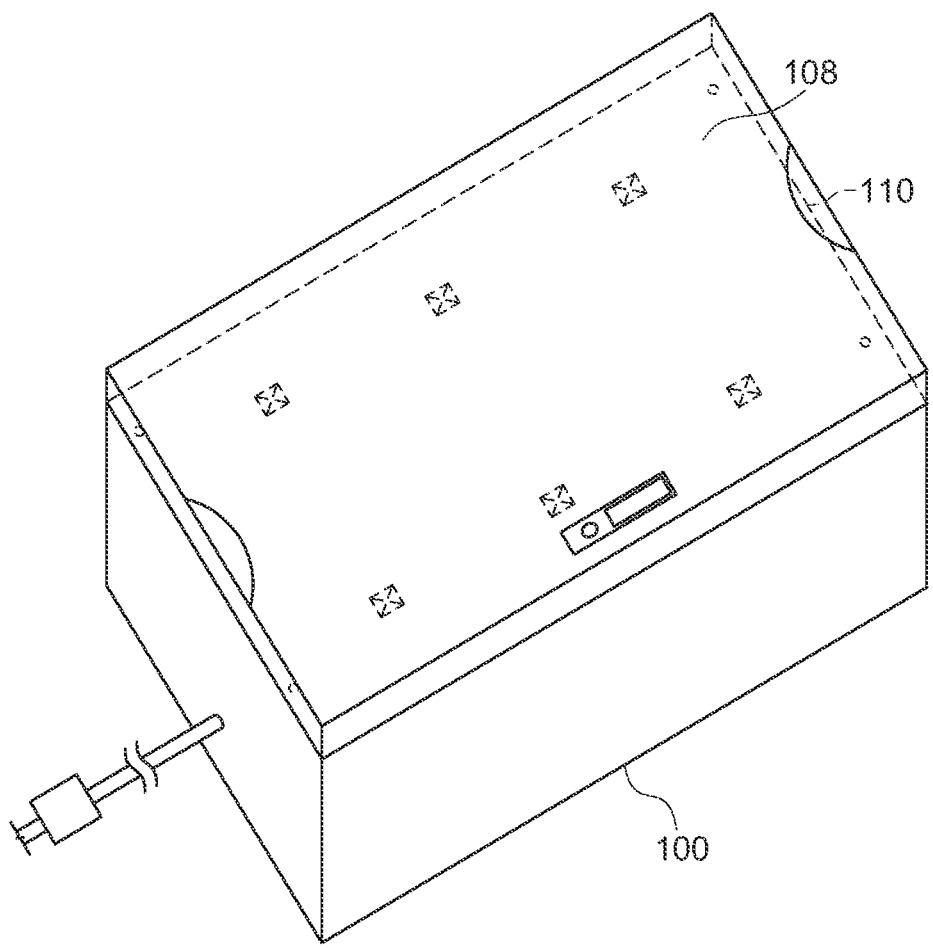
FIG. 3 illustrates a perspective view of a closed portable sanitizing box system in accordance with one embodiment of the present invention.

FIG. 2 illustrates a partially constructed perspective view of a portable sanitizing box 100 in accordance with one embodiment of the present invention. The view of FIG. 2 presents the shelves 104, 106A and 106B, illustrated in FIG. 1 set into the interior volume 102 of the box 100, aligned therein through the use of the rails 112, the set of which maintain alignment of the shelves 104, 106A and 106B within the interior volume 102 of the box 100. FIG. 3 continues the evolution begun in FIGS. 1 and 2 by illustrating a perspective view of a closed portable sanitizing box 100 in accordance with one embodiment of the present invention. When closed, the box 100 meets flush with the door 108 to seal the interior volume of the box and prevent the leakage of UVC light, ozone, or other sanitizing agent from escaping the interior volume of the box 100. When unlocked, the door 108 may be opened through use of the side indentations 110, which provide a convenient point for the operator to grip the door for opening and exposure of objects in the interior volume.

Figure 4:
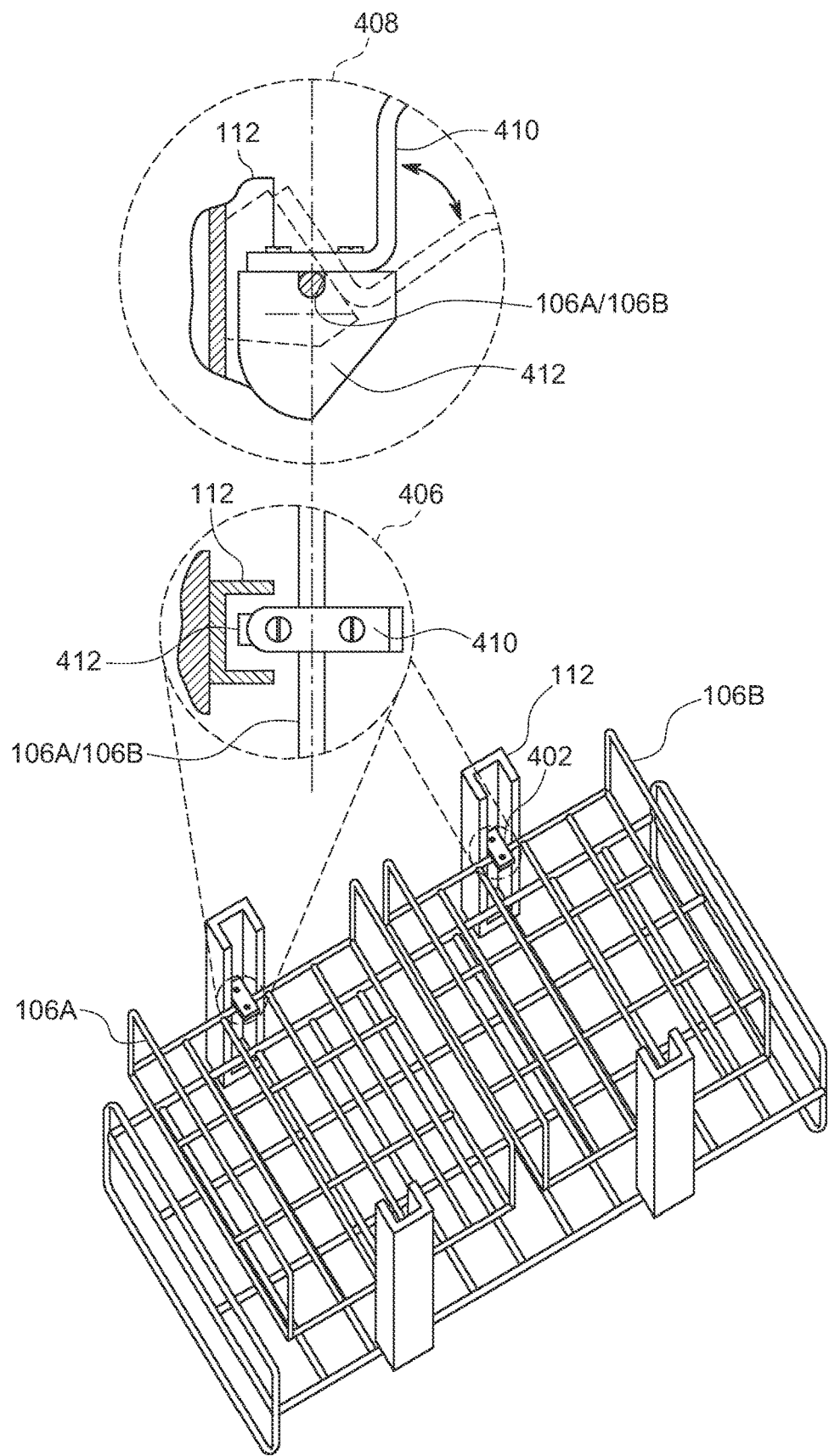
FIG. 4 illustrates a perspective view of the shelf assembly for a portable sanitizing box system in accordance with one embodiment of the present invention.

FIG. 4 illustrates a perspective view of the shelf assembly for a portable sanitizing box system in accordance with one embodiment of the present invention. In particular, the embodiment of FIG. 4 presents the adjustable locking system that the shelves 106A/106B may employ to maintain a specific height that the operator desires, which is shown in detail as a top-down view 406 and cross-sectional view 408. When an operator places a given shelf in the sterilization box, he or she aligns one or more shelf locks 402 into corresponding tracks 112 that may be affixed to the inner walls of the sterilization box. The exemplary shelf lock 402 is built around the framework of the shelves 106A/106B, in this instance built around the wire framework that comprises the shelves 106A/106B. In this exemplary configuration, the locking mechanism is set at a distance between the cross (center of the radius) and center rotation that is slightly bigger than the distance between the watt of the channel and the eccentric in the vertical position. An operator moves the shelf-lock mechanism lever 410 into the locked position by rotating it down (or away from the wall) and having it 412 engage the wall. In the unlocked position, the shelf lock swivels freely with the shelf lock 402 hanging in a vertical position because it is heavier on the bottom.

In operation, the user positions the shelves 106A/106B in the corresponding rails 112 starting at the top opening and lowers it to reach the desired height location. When the desired height is reached, the user manually rotates the shelf lock 402 down to secure the shelf 106A/106B in place against the wall of the rail 112. The shelf-lock mechanism 402 may engage the wall of the rail and locks into place by reducing the radius, which serves to hold the shelves 106A/106B in place. To raise or remove the shelf 106A/106B, the user lifts the shelf 106A/106B with the handles and releases the shelf-lock mechanism 402 by the upward friction motion. This allows the user to quickly remove the shelf without having to manually unlock the shelf-lock mechanism.

Figure 5:
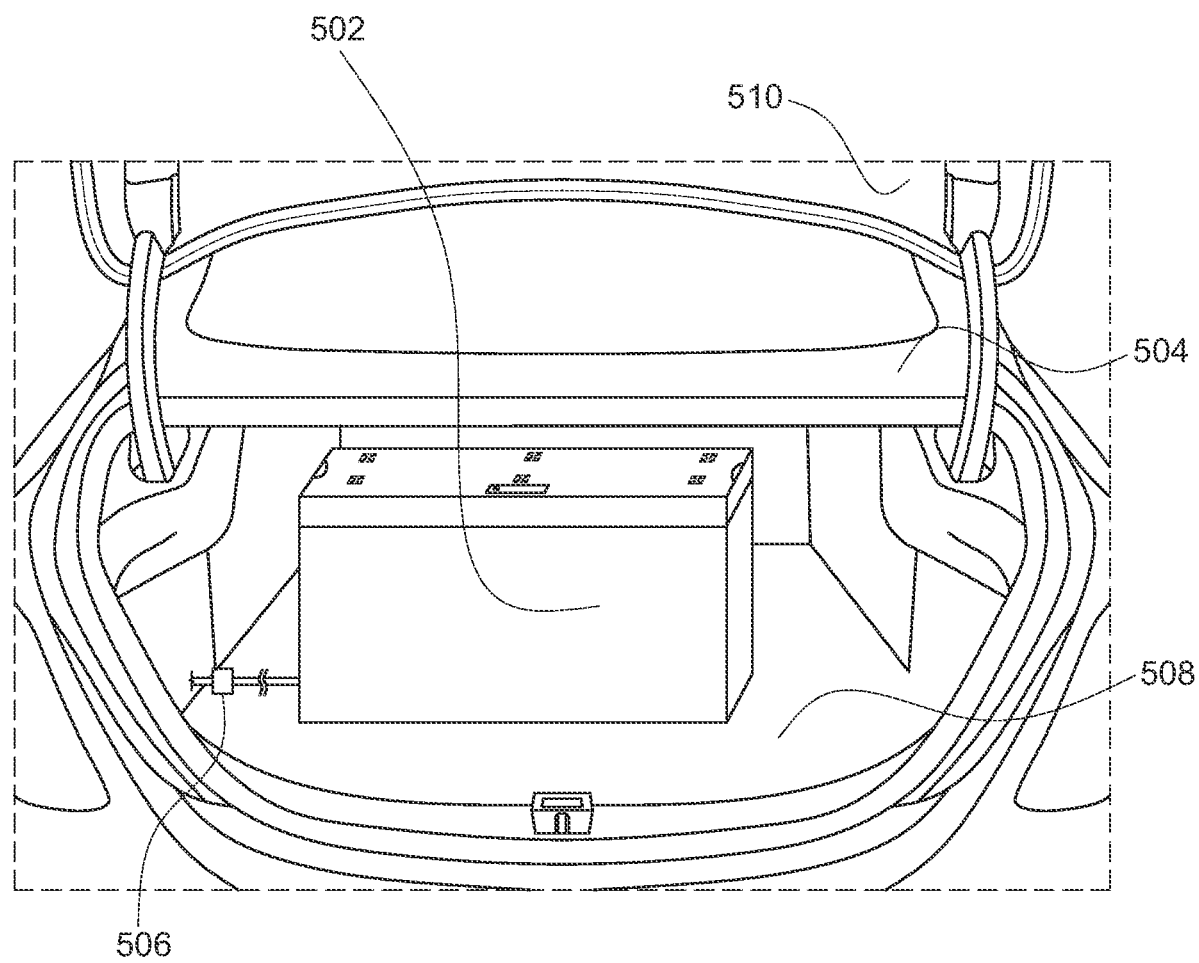
FIG. 5 illustrates one embodiment of a portable sanitizing box disposed within the trunk of a vehicle in accordance with one embodiment of the present invention.

As discussed herein, embodiments of the invention are formed for disposal within or integration with the trunk 508 of a vehicle. FIG. 5 presents a vehicle 504, such as car, truck, SUV, or other vehicle, with an exemplary sanitation box 502 in accordance with the various embodiments of the invention disposed in its trunk 508. The sanitation box 502 may be wired 506 into the power system of the vehicle, which may be configured to provide power to the sanitation box 502 with or without the vehicle 504 being in operation. Power may alternatively be supplied by external batteries or other power source. When the trunk door 510 is closed, the sanitation box 502 is securely enclosed within the vehicle 504 and is therefore safe from tampering. Embodiment also comprise the sanitation box 502 being affixed to a floor of the trunk 508 of the vehicle 504, as well as unaffixed and removeable. When removeable, the wire 506 to the vehicle power system, when present, may comprise a plug or similar removeable connector.

FIGS. 1 through 5 are conceptual illustrations allowing for an explanation of the present invention. Those of skill in the art should understand that various aspects of the embodiments of the present invention could be implemented using different materials, fasteners, and minor design modifications. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention.

In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments, which may be taken alone or in combination, will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but instead should be defined only in accordance with the following claims and their equivalents.

What is claimed is:

1. A box-type-portable sanitizer using UVC radiation device for use in the trunk of a vehicle comprising:
an opaque box with a main body defining an inner space and opening, the opaque box configured for receiving and housing one or more objects, one of more sides of the opaque box covered with a UVC reflective material;
a power source;
a plurality of 275 nm UVC LED SMD 3535 Deep LED lights positioned and mounted between the walls of the box and facing the interior of the box through openings to irradiate the main body of the box at specific intervals within the inner space, the LEDs operative to receive power from the power source and generate UVC light;

a removable lower shelf with minimal opaque components positioned against a bottom of the device and two adjustable half shelves with minimal opaque components positioned within the main body of the box;

one or more pair of rails embedded into the opaque box configured to maintain alignment of and stability for the removable lower shelf and provide adjustability of a respective height of the two removable half shelves;

one or more shelf locks disposed on a given one of the removable lower shelf and two removable adjustable half shelves that engage a corresponding one of the one or more pair of rails, wherein the one or more shelf locks engage the corresponding one of the one or more pair of rails by rotation down and away from a wall of the opaque box; and a safety device embedded into the box to ensure provision of power from the power source to the LEDs only while box is securely closed.

2. The box-type-portable sanitizer of claim 1 further comprising:

one or more ceramic Ozone generators positioned and mounted between the walls of the box, the one or more ceramic Ozone generators configured to receive power from the power source and output ozone into the interior of the box.

3. The box-type-portable sanitizer of claim 1, wherein the safety mechanism comprises an electrical contact on a wall of the box provided in registry with an electrical contact on a removeable lid of the box when closed, wherein the electrical contacts are configured to interrupt the power to the LEDs when the electrical contacts are not physically in contact.

4. The box-type sanitizer of claim 1 wherein the removable lower shelf and the two adjustable half shelves are constructed of a UVC stable material.

5. The box-type sanitizer of claim 1 wherein the removable lower shelf and the two adjustable half shelves are constructed of epoxy-covered steel.

* * * * *